(12) United States Patent
Holvoet Vermaut et al.

(10) Patent No.: US 10,996,490 B2
(45) Date of Patent: May 4, 2021

(54) METHOD FOR TESTING THE FEASIBILITY OF A PAIR OF SPECTACLES

(71) Applicant: ESSILOR INTERNATIONAL, Charenton-le-Pont (FR)

(72) Inventors: Benoit Holvoet Vermaut, Charenton-le-Pont (FR); Luc Martin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 322 days.

(21) Appl. No.: 15/766,616

(22) PCT Filed: Oct. 6, 2016

(86) PCT No.: PCT/FR2016/052584
§ 371 (c)(1),
(2) Date: Apr. 6, 2018

(87) PCT Pub. No.: WO2017/060639
PCT Pub. Date: Apr. 13, 2017

(65) Prior Publication Data
US 2018/0299693 A1   Oct. 18, 2018

(30) Foreign Application Priority Data
Oct. 9, 2015   (FR) ...................................... 1559651

(51) Int. Cl.
*G02C 7/00* (2006.01)
*G02C 7/02* (2006.01)
(Continued)

(52) U.S. Cl.
CPC ................ *G02C 7/027* (2013.01); *A61B 3/10* (2013.01); *A61B 3/111* (2013.01); *G02C 7/028* (2013.01);
(Continued)

(58) Field of Classification Search
CPC ...... G02C 7/027; G02C 13/003; G02C 7/028; G02C 2202/08; G02C 7/024; G02C 7/025; A61B 3/10; A61B 3/111
(Continued)

(56) References Cited

U.S. PATENT DOCUMENTS

2003/0123026 A1\* 7/2003 Abitbol ................ G02C 13/005
351/204
2010/0293192 A1\* 11/2010 Suy ...................... G02C 13/003
707/769
(Continued)

FOREIGN PATENT DOCUMENTS

EP    1 468 649 A1   10/2004
FR      2885231 A1 \* 11/2006 ........... G02C 13/003
(Continued)

OTHER PUBLICATIONS

International Search Report, dated Jan. 4, 2017, from corresponding PCT/FR2016/052584 application.

*Primary Examiner* — William R Alexander
*Assistant Examiner* — Henry A Duong
(74) *Attorney, Agent, or Firm* — Nixon & Vanderhye (57) ABSTRACT

Disclosed is a method for testing the feasibility of a pair of spectacles, the pair of spectacles comprising an identified spectacle frame. The method includes steps of: a) acquiring a range of values of at least one first parameter relating to a spectacle wearer, in all of which range it is desired to ensure the feasibility of the pair of spectacles, b) acquiring a range of values of at least one second parameter that relates to a spectacle wearer and that is different from each first parameter, in all of which range it is desired to ensure the feasibility of the pair of spectacles, c) confirming, for a characteristic number of values of each second parameter,
(Continued)

that the pair of spectacles is feasible whatever the value of each first parameter comprised in its range.

20 Claims, 4 Drawing Sheets

(51) Int. Cl.
    *A61B 3/10*     (2006.01)
    *G02C 13/00*     (2006.01)
    *A61B 3/11*     (2006.01)

(52) U.S. Cl.
    CPC ....... *G02C 13/003* (2013.01); *G02C 2202/08* (2013.01)

(58) Field of Classification Search
    USPC .................................................. 351/159.75
    See application file for complete search history.

(56) References Cited

U.S. PATENT DOCUMENTS

2013/0231941 A1*   9/2013   Pham ..................... G06Q 50/22
                                                                                             705/2
2016/0327815 A1    11/2016   Rego et al.

FOREIGN PATENT DOCUMENTS

| FR | 2 910 647 A1 | 6/2008 |
|----|--------------|--------|
| FR | 3 016 052 A1 | 7/2015 |
| FR | 2 885 231 A1 | 11/2016 |

\* cited by examiner

METHOD FOR TESTING THE FEASIBILITY OF A PAIR OF SPECTACLES

TECHNICAL FIELD OF THE INVENTION

The present invention relates generally to the field of eyewear.

It relates more particularly to a process for testing the feasibility of a pair of spectacles, that is to say that makes it possible to verify a priori the possibility of assembling a pair of spectacles.

TECHNOLOGICAL BACKGROUND

The technical part of the work of an optician consists in fitting a pair of corrective ophthalmic lenses in a spectacle frame selected by a wearer.

This fitting is broken down into three main operations:
acquiring the geometry of a longitudinal profile representative of the shape of the outline of one of the eye wires of the selected spectacle frame,
centering the ophthalmic lens in question, which consists in suitably positioning and orienting this longitudinal profile on the lens so that once the lens edged following this longitudinal profile then fitted in its frame, it is correctly positioned relative to the corresponding eye of the wearer so that it can fulfill as best as possible the optical function for which it was designed, then
edging the lens, which consists in machining its outline to the shape of the longitudinal profile.

By way of example, interest may more particularly be taken in the case of rimmed spectacle frames. In frames of this type, the eye wire (or "rim") is designed to surround the whole of the periphery of the lens. For holding the lens, it comprises an inner groove referred to as a rim groove.

The acquiring operation then consists in feeling the outline of the rim groove to determine the shape thereof. As for the edging operation, it consists in edging and beveling the edge face of the lens to reveal therein an interlocking rib that can interlock in the rim groove.

Unfortunately, sometimes certain spectacle frames are not compatible with all ophthalmic lenses and the assembly is not able to be carried out.

An example that clearly illustrates this problem is that of highly curved ophthalmic lenses, which cannot interlock in the rims of spectacle frames that are not highly curved.

Another example is that of people whose eyes are very close together, for whom the pupillary point (that is to say the point of the lens opposite which the eye of the wearer will be found) will be very off-centered relative to the center of the eye wire of the spectacle frame. In this case, it will be necessary to use a large diameter ophthalmic lens. Yet, for certain power prescriptions, the available lens diameter is reduced (otherwise the lenses would be too thick at the edge and at the center). Fitting may thus be impossible.

Sometimes the optician only becomes aware of this impossibility of fitting the ophthalmic lens in the spectacle frame when assembling the pair of spectacles. In this eventuality, the optician is then forced to call back the customer to ask him/her to choose another frame.

If he/she has enough experience, the optician may avoid this problem by offering, when the wearer comes to choose his/her spectacle frame, only a small sample of frames for which he/she estimates that it will be possible to fit ophthalmic lenses (considering the prescription of the wearer and the shape of his/her face). This sample is then generally smaller than it should be since the optician cannot exactly estimate which are the spectacle frames that will be usable. The drawback is then that the wearer is offered a very limited number of spectacle frames.

OBJECTIVE OF THE INVENTION

In order to overcome the aforementioned drawbacks of the prior art, the present invention provides a method that makes it possible to automatically determine to what extent a pair of spectacles will be able to be assembled.

More particularly, according to the invention a testing process is provided as defined in the introduction, wherein provision is made for steps consisting in:

a) acquiring a range of values of at least one first parameter relating to a spectacle wearer, in the whole of which range it is desired to ensure the feasibility of the pair of spectacles, b) acquiring a range of values of at least one second parameter relating to a spectacle wearer, in the whole of which range it is desired to ensure the feasibility of the pair of spectacles, c) verifying, for a characteristic number of values of each second parameter, that the pair of spectacles is feasible irrespective of the value of each first parameter included in its range.

Thus, by means of the invention, for each spectacle frame, it will be possible to know to what extent this frame could receive the ophthalmic lenses of a wearer, by simply determining the values of the first and second parameters and by verifying that they belong to the ranges of values for which the pair of spectacles has been qualified as "feasible".

Other advantageous and nonlimiting features of the testing process in accordance with the invention are the following:

said first and second parameters are ophthalmic, morphological or geometric-morphological parameters characterizing spectacle wearers;

said first and second parameters are chosen from the following list: spherical refractive power, cylindrical refractive power, pupillary height, pupillary distance or half-pupillary distance;

in step a), a range of values of two first parameters is acquired, and, in step c), it is verified, for a characteristic number of values of each second parameter, that the pair of spectacles is feasible irrespective of the values of the two first parameters included in their range;

in step b), a range of values of two second parameters is acquired, and, in step c), it is verified, for a characteristic number of pairs of values of the second parameters, that the pair of spectacles is feasible irrespective of the value of the first parameter included in its range;

in step c), a degree of feasibility of the pair of spectacles is evaluated, said degree of feasibility possibly taking at least three different values;

provision is made, prior to step a), for a step of acquiring curvature data of the spectacle frame and, in step a), the first parameter being a spherical refractive power or cylindrical refractive power, the range of values of the first parameter is chosen as a function of said curvature data of the spectacle frame;

considering a subrange of the range of values of each second parameter wherein the pair of spectacles is not feasible, provision is made for a step d) consisting in verifying, for a characteristic number of values of each first parameter, that the pair of spectacles is feasible irrespective of the value of each second parameter included in said subrange;

considering a subrange of the range of values of each second parameter wherein the pair of spectacles is feasible and a subrange encompassing the range of values of the first parameter, provision is made for a step d) consisting in verifying, for a characteristic number of values of the first parameter included in said subrange, that the pair of spectacles is feasible irrespective of the value of each second parameter included in said subrange.

The invention also relates to a method for classifying spectacle frames, by means of a database comprising entries each associated with a spectacle frame, comprising a computing operation during which the testing process as claimed in one of the preceding claims is implemented for an identified spectacle frame, and a storage operation during which the range of values of each first parameter and also a range of values of each second parameter in the whole of which the pair of spectacles is feasible is recorded in a new entry of the database associated with said identified spectacle frame.

Preferentially, provision is made for an operation for acquiring a first particular value of the first parameter and a second particular value of the second parameter, these first and second values corresponding to a given spectacle wearer, and an operation for selecting entries of said database wherein the ranges stored comprise said first and second particular values.

The invention also relates to a catalogue of spectacle frames available for manufacturing pairs of spectacles, comprising, for each spectacle frame:
an identifier of the spectacle frame,
a range of values of at least one first parameter relating to a spectacle wearer,
a range of values of at least one second parameter relating to a spectacle wearer, and which is different from each first parameter,
said ranges of values being defined in such a way that it is possible to manufacture a pair of spectacles with said spectacle frame irrespective of the values of the first and second parameters included in their ranges.

The invention finally relates to an indicator of feasibility of a pair of spectacles by means of an identified spectacle frame, which indicator is calculated as a function of:
a range of values of at least one first parameter relating to a spectacle wearer,
a range of values of at least one second parameter relating to a spectacle wearer, and which is different from each first parameter, said ranges of values being defined in such a way that it is possible to manufacture a pair of spectacles with said spectacle frame irrespective of the values of the first and second parameters included in their ranges.

DETAILED DESCRIPTION OF AN EXEMPLARY EMBODIMENT

The description which follows with reference to the appended drawings, which are given by way of nonlimiting examples, will make it easy to understand what the invention consists of and how it can be achieved.

Figures 1, 3:
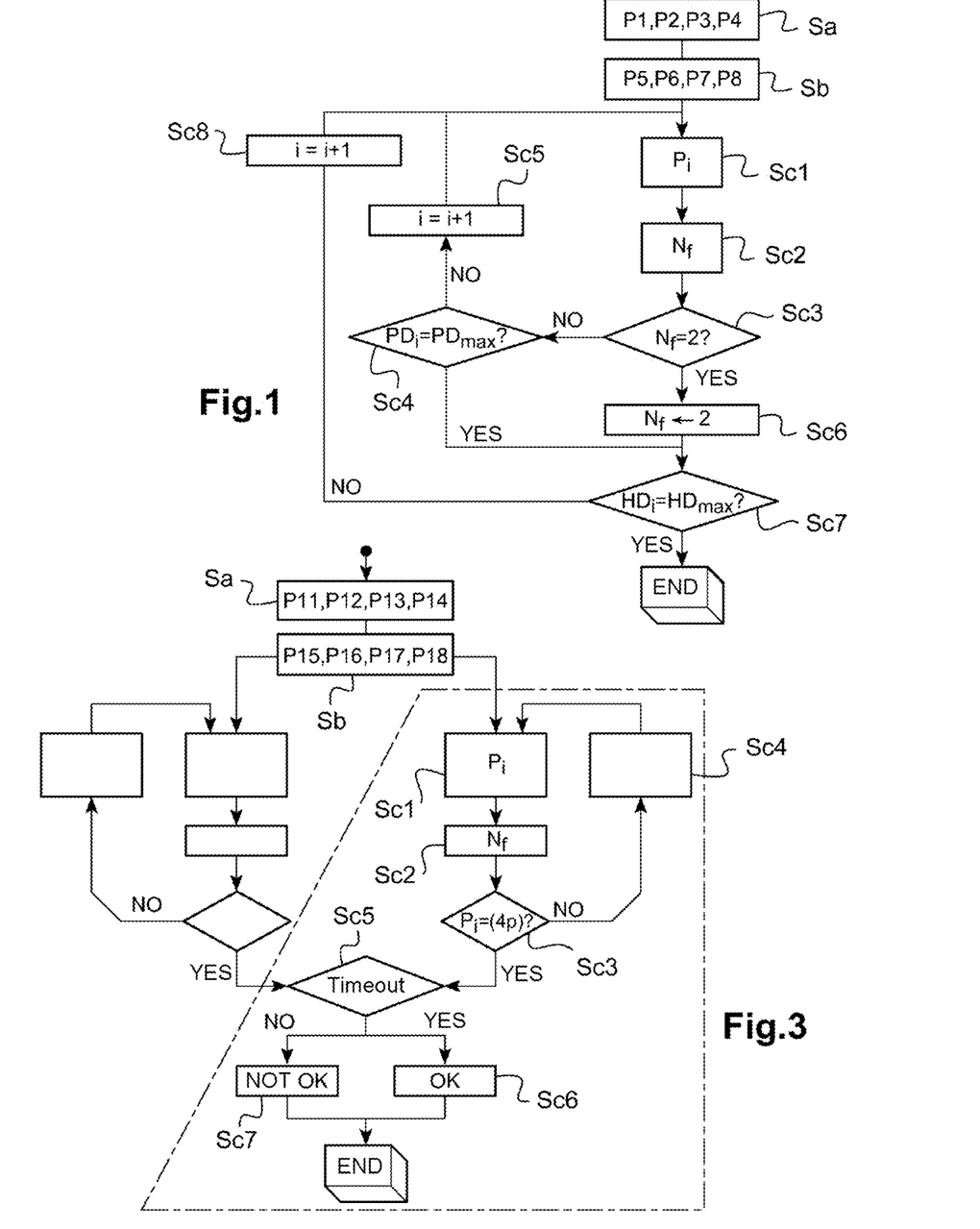
FIG. 1 is a flowchart illustrating the steps of an algorithm enabling the implementation of a first embodiment of the testing process in accordance with the invention.
FIG. 3 is a flowchart illustrating the steps of an algorithm enabling the implementation of a second embodiment of the testing process in accordance with the invention.

In FIGS. 1 and 3, two flowcharts have been represented that illustrate the steps enabling the implementation of two embodiments of a process for testing the feasibility of a pair of spectacles.

Conventionally, a pair of spectacles comprises a spectacle frame, and two ophthalmic lenses. A pair of spectacles is said to be feasible (or "assemblable") when it is possible to fit the two ophthalmic lenses in the spectacle frame, in such a way that the whole assembly is solid and attractive.

The objective of the testing process is to verify a priori which ophthalmic lenses could be fitted in a previously identified spectacle frame, and which ophthalmic lenses could not be fitted therein (unless optionally defects in the assembly of the frame and lenses are tolerated).

This process will be able to be carried out by any type of electronic and/or computer device.

Here, it will be carried out by a calculator such as a computer, comprising a processor (CPU), a random-access memory (RAM), a read-only memory (ROM), and various input and output interfaces.

By means of its input interfaces, the calculator is suitable for receiving input signals originating from various acquisition means. An acquisition means could be a touchscreen or a keyboard, enabling the user to enter information. Another acquisition means could be a device for determining the shape of the spectacle frame. The input signals could then be related to the shape of the spectacle frame and to the information entered by the user.

For its part, the read-only memory stores data used in the context of the testing process described below.

As will become clearly apparent in the remainder of this disclosure, it stores in particular a database register, which comprises several entries each associating, with a spectacle frame reference, ranges of values that indicate to what extent an ophthalmic lens is "fittable" in this spectacle frame.

It also stores a computer application, consisting of computer programs comprising instructions, the execution of which by the processor enables the implementation, by the calculator, of the process described hereinbelow.

The spectacle frame used in the context of the process described hereinbelow is "identified" in the sense that the testing process is applied to a spectacle frame having main characteristics that are known.

Figure 2:
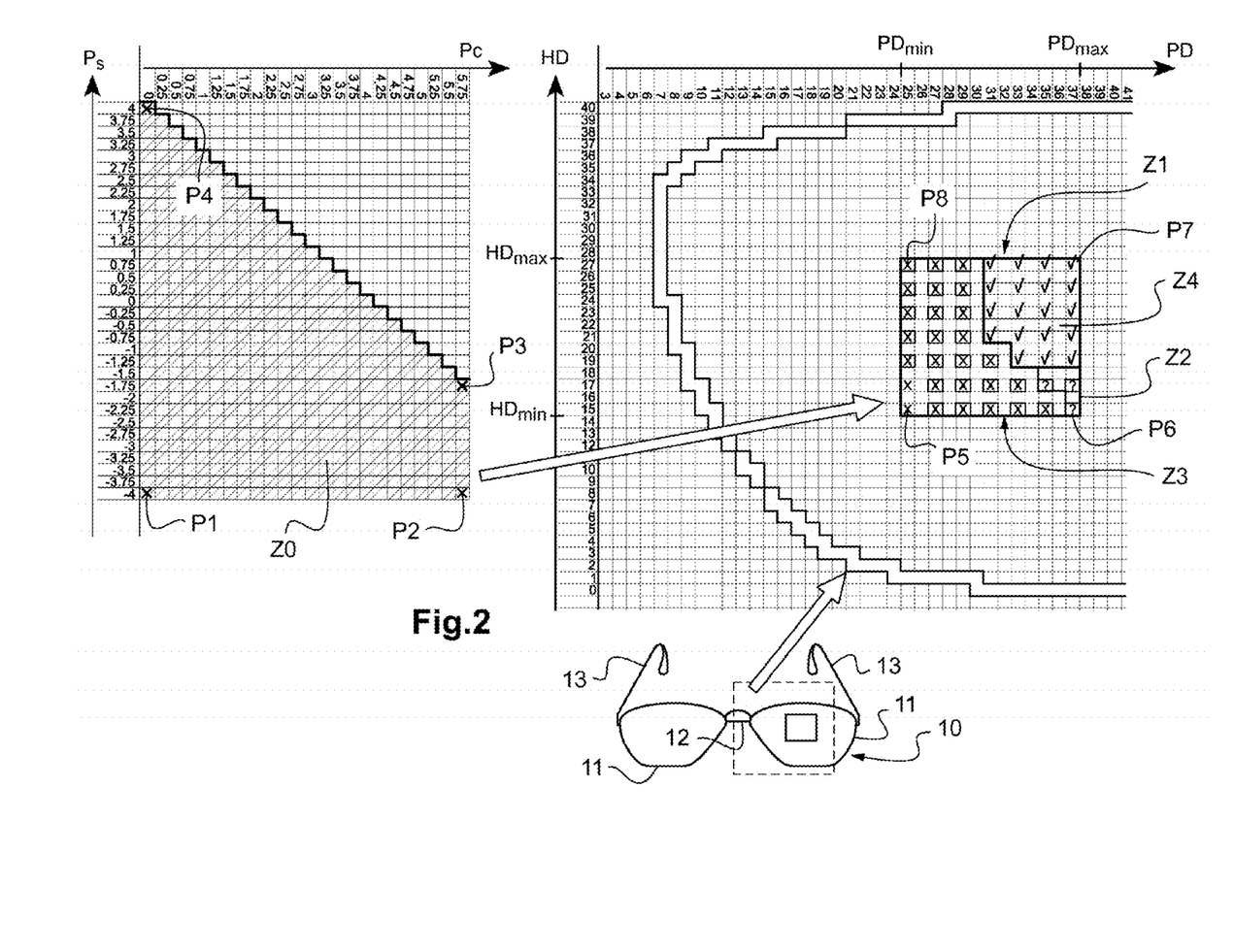
FIG. 2 represents two graphs illustrating the ranges of the first and second parameters used in the context of the testing process from FIG. 1.

This spectacle frame could be of any type. As is represented at the bottom of FIG. 2, it is a rimmed spectacle frame, that is to say a spectacle frame comprising two rigid eye wires 11 (or "rims") connected together by a bridge 12 and each bearing an arm 13. Each of these two eye wires 11 internally has a groove (or "rim groove") in which a rib (or "bevel") running along the edge face of the ophthalmic lens is intended to interlock.

Here, among the main characteristics of the spectacle frame 10, at least the distance between the two eye wires 11 and the shape of the rim groove of each eye wire 11 are known.

As a variant, it could be another type of spectacle frame. By way of nonlimiting example, it could be a half-rimmed frame (each eye wire of which comprises a rigid upper arc and a wire that is provided to pass underneath the lens) or a rimless frame (the bridge and the arms of the frame then comprising means for fastening through holes provided in the lenses).

Each ophthalmic lens capable of being fitted in the spectacle frame 10 may be defined by geometric characteristics (initial diameter, center thickness, etc.) and by optical characteristics.

These optical characteristics define the optical corrective power. They are expressed in the form of spherical, cylindrical and prismatic refractive properties.

It is understood that such an optical definition covers a more general scope than a purely surface definition: it defines in its entirety the refractive effect of the lens on an incident light ray, resulting from the algebraic sum of the refraction carried out successively on the front and rear faces of the lens.

Among these refractive properties, the "spherical refractive power" of a lens is firstly defined for an incident ray beam passing through this lens (also referred to as total power or refractive power or focusing power or spherical optical power), as the value that characterizes and quantifies the first spherical refractive effect ("magnifying glass" effect) of the lens on the ray beam in question: if it is positive, the lens has a convergent effect on the ray beam; if it is negative, the effect on the ray beam is divergent. The point of the lens where the magnifying glass effect is zero (i.e., in the case of a lens having an exclusively spherical optical power, the point where the incident ray and the transmitted ray have the same axis) is referred to as the optical center.

Furthermore, the "cylindrical refractive power" of a lens is defined for an incident ray passing through this lens (also referred to as cylindrical optical power) as the value that characterizes and quantifies the cylindrical refractive effect exerted by the lens on the ray in question, according to which it forms not only one but two focal spots, located in different planes, which are generally perpendicular to one another and are referred to as tangential focal line and sagittal focal line. This cylindrical power, also referred to as "astigmatism power" or simply "astigmatism", corresponds to the difference in the spherical powers between the two focal spots. The two spots are identified by an axis that passes through their "optical center" commonly referred to as the cylinder axis.

Finally, the "prismatic refractive power" of a lens is defined for an incident ray passing through this lens (also referred to as prismatic optical power) as the value that characterizes and quantifies the prismatic refractive effect, or more simply deviation effect, exerted by the lens on the ray in question. This prismatic power, also referred to as "prism", corresponds to the deviation angle of the ray, i.e. the angle formed between the entering and exiting portions of the ray. The prism is broken down into two components: one horizontal, referred to as horizontal prism, corresponding to the angle formed between the projections of the entering and exiting portions of the ray in the horizontal plane, the other vertical, referred to as vertical prism, corresponding to the angle formed between the projections of the entering and exiting portions of the ray in the vertical plane.

In the remainder of this disclosure, the term "wearer" will be applied to any person capable of wearing the spectacle frame 10. At the moment when the testing process according to the invention is implemented, this person might not yet be identified.

The "half-pupillary distances PD" of the wearer are defined as the distances between the bridge of the nose of the wearer and each of his/her pupils.

The "pupillary heights HD" of the wearer wearing the spectacle frame 10 are also defined as the distances that vertically separate his/her pupils from a horizontal line passing through the lowest points of the two eye wires of the spectacle frame 10.

According to one particularly advantageous feature of the invention, the process for testing the feasibility of the fitting of an ophthalmic lens to the spectacle frame 10 comprises the following three steps:

a) acquiring a first range of values of at least one first parameter relating to the wearer, in the whole of which range it is desired to ensure the feasibility of the pair of spectacles, b) acquiring a second range of values of at least one second parameter which relates to the wearer and which is different from each first parameter, in the whole of which range it is desired to know whether the pair of spectacles is feasible, c) verifying, for a characteristic number of values of the second range, that the pair of spectacles is feasible irrespective of the value of each first parameter included in its range.

By way of illustration, an example of implementation of this process could be the following:

a) acquiring the minimum and maximum limits of a spherical refractive power range, in the whole of which range it is desired for the pair of spectacles to be feasible (irrespective of the values of the other parameters), b) acquiring the minimum and maximum limits of a cylindrical refractive power range, and c) verifying, for a characteristic number of cylindrical refractive power values included between the minimum and maximum limits, if the pair of spectacles is feasible irrespective of the value of the spherical refractive power (as long as the latter remains between its minimum and maximum limits).

In this way, in order to know if a pair of spectacles is feasible, the user will only have to verify whether the spherical and cylindrical refractive powers are included in the ranges identified.

However, the number of parameters to be taken into account in order for the process to have reliable results should advantageously be increased.

Thus, preferentially:
in step a), two first parameters are considered, the values of which are included in a first range,
in step b), two second parameters are considered, the values of which are included in a second range, and
in step c), it is verified, for a characteristic number of pairs of values of the second parameters, that the pair of spectacles is feasible irrespective of the values of the two first parameters.

It will be specified here that a range of values may be formed by a single point (i.e. by a single doublet of values), by a set of points, or by an infinity of points between end points.

As a variant, it would be possible to consider more parameters.

Here, the first and second parameters are ophthalmic, morphological or geometric-morphological parameters characterizing the spectacle wearer.

An ophthalmic parameter is a parameter relating to the vision characteristics of one of the eyes of the spectacle wearer. Typically, this ophthalmic parameter may be expressed in the form of a refractive power that it is necessary to provide to an ophthalmic lens in order to correct a vision defect of the wearer.

A morphological parameter is a parameter relating to the shape of the face of the spectacle wearer. Typically, a half-pupillary distance constitutes one such morphological parameter.

A geometric-morphological parameter is a parameter that depends not only on the shape of the face of the wearer but also on the shape of the spectacle frame 10. Typically, a pupillary height constitutes one such geometric-morphological parameter.

In the embodiments described in the remainder of this disclosure, the parameters taken into account will be:
the spherical refractive power Ps,
the cylindrical refractive power Pc,
the pupillary height HD,
the half-pupillary distance PD.

Specifically, it is considered here that the "assemblable" nature of a pair of spectacles results from a compromise between the values of these four parameters, taking into account the shape of the identified spectacle frame 10.

Indeed it is understood that the spherical refractive power Ps and cylindrical refractive power Pc values have an influence on the shape of the ophthalmic lens and therefore on the feasible nature of the pair of spectacles. By way of example, an ophthalmic lens that is very thick at its peripheral edge, or on the contrary very thin, will thus not be able to be fitted in just any spectacle frame. A highly curved ophthalmic lens will furthermore not be able to be fitted in a flat spectacle frame, and vice versa.

The pupillary height HD and half-pupillary distance PD values furthermore have an influence on the position of the ophthalmic lens in the eye wire of the spectacle frame 10 and therefore on the feasible nature of a pair of spectacles. Specifically, it is understood that an ophthalmic lens well centered in the eye wire will have a thickness at its edges which will vary little, whereas a very off-centered lens will have a width that will vary substantially, with the risk that this thickness is locally too thin or too thick to enable the fitting of the ophthalmic lens in the spectacle frame.

As a variant, other parameters could also be considered, such as the prismatic refractive power, since it also has an influence on the thickness of the ophthalmic lens along its peripheral edge.

To better understand the invention, a first embodiment of the testing process may now be described in greater detail, with reference to FIGS. 1 and 2.

During step a) (denoted Sa in FIG. 1), the calculator acquires the first range of values, denoted Z0.

This first range Z0, clearly illustrated on the left-hand part of FIG. 2, corresponds to a range of doublets of values within which it is desired for the pair of spectacles to be feasible.

Here, the first parameters are the cylindrical refractive power Pc and the spherical refractive power Ps. Each doublet then comprises, on the x-axis, a cylindrical power Pc value and, on the y-axis, a spherical refractive power Ps value. Each doublet will then be able, in the remainder of this disclosure, to be denoted by the term "point" in the sense that it has an x-coordinate and a y-coordinate.

In this first embodiment of the testing process, it is desired to be able to fit in the spectacle frame 10 any ophthalmic lens having a spherical refractive power Ps and a cylindrical refractive power Pc, the values of which are included in the first range Z0.

In FIG. 2, it is observed that the first range Z0 is between four end points P1, P2, P3, P4.

Here, by way of illustration, these four end points P1, P2, P3, P4 are defined in the following manner:
at point P1, Pc=0 δ and Ps=−4 δ (or "diopters"),
at point P2, Pc=5.75 δ and Ps=−4 δ,
at point P3, Pc=5.75 δ and Ps=−1.75 δ,
at point P4, Pc=0 δ and Ps=4 δ.

This first range Z0 then comprises all the doublets (Pc, Ps) located in the quadrilateral, the corners of which correspond to the four end points P1, P2, P3, P4.

The first range Z0 is here discretized by intervals of 0.25 δ.

During step b) (denoted Sb in FIG. 1), the calculator acquires the second range Z1.

This second range Z1, clearly illustrated on the right-hand part of FIG. 2, corresponds to a range of doublets of values within which it is desired to verify whether or not the pair of spectacles is feasible.

Here, the second parameters are the pupillary height HD and the half-pupillary distance PD. Each doublet then comprises, on the x-axis, a half-pupillary distance PD value and, on the y-axis, a pupillary height HD value.

In this first embodiment of the testing process, it is desired to be able to determine, in this second range Z1, which are the doublets of values (PD, HD) for which it will be possible to fit an ophthalmic lens in the spectacle frame 10, irrespective of the spherical refractive power Ps and cylindrical refractive power Pc values of this lens included in the first range Z0.

In FIG. 2, it is observed that the second range Z1 is between four end points P5, P6, P7, P8.

Here, by way of illustration, these four end points P5, P6, P7, P8 are defined in the following manner:
at point P5, HD=15 mm and PD=25 mm,
at point P6, HD=15 mm and PD=37 mm,
at point P7, HD=27 mm and PD=37 mm,
at point P8, HD=27 mm and PD=25 mm.

This second range Z1 then comprises all the doublets (PD, HD) located in the square, the corners of which correspond to the four end points P5, P6, P7, P8.

The second range Z1 is here discretized by intervals of 1 mm. In other words, in the second range Z1 only a limited number of discretized points will be considered.

As for step c), it is performed in several successive and iterative operations, denoted Sc1 to Sc8 in FIG. 1.

This step c) consists in evaluating, for each discretized point of the second range Z1, a degree of feasibility Nf of the pair of spectacles.

This degree of feasibility could take at least two values, for example 0 or 1 depending on whether or not the pair of spectacles is feasible.

Here, this degree of feasibility Nf could take three different values, depending on whether the pair of spectacles is feasible, is not feasible, or is feasible on condition that fitting imperfections are accepted.

As a variant, this degree of feasibility could take more values.

The first operation Sc1 of step c) consists in determining the point $P_i$ to be examined, among the discretized points of the second range Z1. This point $P_i$ comprises coordinates denoted $(PD_i, HD_i)$.

Initially (for i=0), the coordinates ($PD_0$, $HD_0$) of the point $P_0$ are coincident with those of the end point P5.

The second operation Sc2 consists in determining whether, for this point $P_i$ to be examined, the fitting of an ophthalmic lens (the spherical refractive power Ps and cylindrical refractive power Pc of which are included in the first range Z0) in the spectacle frame 10 is possible.

In practice, this second operation Sc2 is carried out by calculating whether this fitting is possible when the spherical refractive power Ps and cylindrical refractive power Pc of the lens are equal to the coordinates of the end point P1, then to those of the end point P2, then to those of the end point P3, and finally to those of the end point P4.

Specifically, it is considered that if these four conditions are met, the pair of spectacles will be feasible irrespective of the spherical refractive power Ps and cylindrical refractive power Pc values included in the first range Z0.

Each of these four calculations is carried out by means of a mathematical function f, which depends on:
- the shape of the eye wire 11 of the spectacle frame,
- the spherical refractive power Ps and cylindrical refractive power Pc values at the end point in question,
- the pupillary height HD and half-pupillary distance PD values at the point $P_i$ to be examined, and
- on the type of material used for the manufacture of the lenses.

By way of illustrative example, this function f may be a polynomial function, the terms of which are constituted by the four aforementioned variables, and the coefficients of which are adjusted depending on the desired tolerances.

More specifically, the values of the coefficients could be set by default as equal to 1, and could then be adjusted if necessary, depending on the requirements of the lens manufacturer and/or of the optician. Thus, these values could be different depending on the range level of the pair of spectacles: specifically, a top-of-the-range pair of spectacles must not suffer from any defect whereas a middle-of-the-range pair of spectacles could have minor defects.

In practice, this function f will still make it possible to make a selection between various assemblies of pairs of spectacles, and the optician will be able to choose, among these assemblies, those that he/she considers to be acceptable or unacceptable.

Here, the result of this function f makes it possible to obtain the degree of feasibility Nf of the pair of spectacles at the point $P_i$ to be examined.

The calculator will thus be able to allocate the value 0, 1 or 2 to the degree of feasibility Nf depending on the result of the function f.

This degree of feasibility Nf may thus be equal to zero (which is illustrated by a cross in the right-hand part of FIG. 2), which then means that it is not a priori possible (or not desirable) to assemble a pair of spectacles for a wearer having a pupillary height HD and a half-pupillary distance having values that correspond to the coordinates of the point $P_i$ to be examined, irrespective of the spherical refractive power Ps and cylindrical refractive power Pc values included in the first range Z0.

The degree of feasibility Nf may be equal to one (which is illustrated by a question mark in the right-hand part of FIG. 2), which then means that it is a priori possible to assemble such a pair of spectacles, on condition that the wearer and/or the optician are/is willing to accept an assembly that is imperfect (in esthetic terms or in terms of solidity of assembly).

Finally, the degree of feasibility may be equal to two (which is illustrated by ticked boxes in the right-hand part of FIG. 2), which then means that it is a priori possible to assemble such a pair of spectacles, while ensuring a perfect assembly.

The third operation Sc3 consists in testing if the degree of feasibility Nf is equal to 2.

If this is not the case, the calculator performs an operation Sc4 that consists in testing if the half-pupillary distance $PD_i$ of the point $P_i$ to be examined is equal to the maximum half-pupillary distance $PD_{max}$ of the second range Z1.

If the half-pupillary distance $PD_i$ is not equal to the maximum half-pupillary distance $P_{max}$ the calculator performs an operation Sc5 which consists in incrementing the subscript i and also the value of the half-pupillary distance $PD_{i+1}$ of the point $P_{i+1}$ to be examined (here by 1 mm). The step Sc1 and the following steps may then be repeated, by considering at step Sc1 the new point $P_{i+1}$ to be examined.

On the other hand, if the half-pupillary distance $PD_i$ is equal to the maximum half-pupillary distance $P_{max}$, the calculator performs an operation Sc7 described below.

At the end of the operation Sc3, if the degree of feasibility Nf is equal to 2, the calculator performs an operation Sc6 which consists in allocating the value 2 to the degree of feasibility Nf of each of the points of the second range Z1 of which:
- the HD y-coordinate is equal to the $HD_i$ y-coordinate of the point $P_i$ to be examined, and of which
- the PD x-coordinate is greater than the $PD_i$ x-coordinate of the point $P_i$ to be examined.

Following this operation Sc6, the calculator performs the operation Sc7.

This operation Sc7 consists in verifying if the pupillary height $HD_i$ of the point $P_i$ to be examined is equal to the maximum pupillary height $HD_{max}$ of the second range Z1.

If this is the case, the process comes to an end.

On the other hand, if this is not the case, the calculator performs an operation Sc8 which consists in incrementing the subscript i, in incrementing the value of the pupillary height $HD_{i+1}$ of the point $P_{i+1}$ to be examined (here by 1 mm), and in bringing the value of the half-pupillary distance $PD_{i+1}$ to the value of the minimum half-pupillary distance $PD_{min}$ (here 25 mm). The step Sc1 and the following steps may then be repeated, by considering at step Sc1 the new point $P_{i+1}$ to be examined.

At the end of this algorithm, the second range Z1 is split into three different zones, including a first zone Z3 in which the fitting of the pair of spectacles is not possible, a second zone Z2 in which the fitting of the pair of spectacles is possible on condition that the user is willing to accept that the assembly is not perfect, and a third zone Z4 in which the fitting of the pair of spectacles is possible.

In this way, when a new wearer appears and wishes to buy a pair of spectacles on the basis of the spectacle frame 10, it will be possible to confirm to him/her very rapidly if his/her pair of spectacles will be able to be assembled, by simply verifying whether his/her prescriptions (in terms of spherical refractive power Ps and cylindrical refractive power Pc) are included in the first range Z0 and whether his/her pupillary height HD and half-pupillary distance PD are included in the zone Z4 of the second range Z1.

If his/her pupillary height HD and half-pupillary distance PD are included in the zone Z2 of the second range Z1, the user could suggest that the new wearer either chooses another spectacle frame, or keeps this choice of frame while accepting however that his/her assembled pair of spectacles has some fitting imperfections.

Finally, it could be noted that the values of the end points P1, P2, P3, P4 delimiting the first range Z0 could be determined either randomly, according to the wishes of the user, or automatically, on the basis of the shape of the spectacle frame 10.

Indeed, it is understood that depending on the shape (and in particular on the curvature) of the spectacle frame 10, it will not be esthetically pleasing or possible to fit just any ophthalmic lens therein.

In that case, during a step prior to step a), the calculator could perform a step of acquiring a characteristic value of the general curvature of the spectacle frame 10, then, in step a), it could determine the values of the coordinates of the end points P1, P2, P3, P4 as a function of this characteristic value.

By way of nonlimiting example, when the spectacle frame is particularly curved, it will be possible to limit the range Z0 to positive spherical power values.

A second embodiment of the testing process in accordance with the invention may now be described, with reference to FIGS. 3 and 4.

During step a) (denoted Sa in FIG. 3), the calculator acquires the first range of values, denoted Z10.

Figure 4:
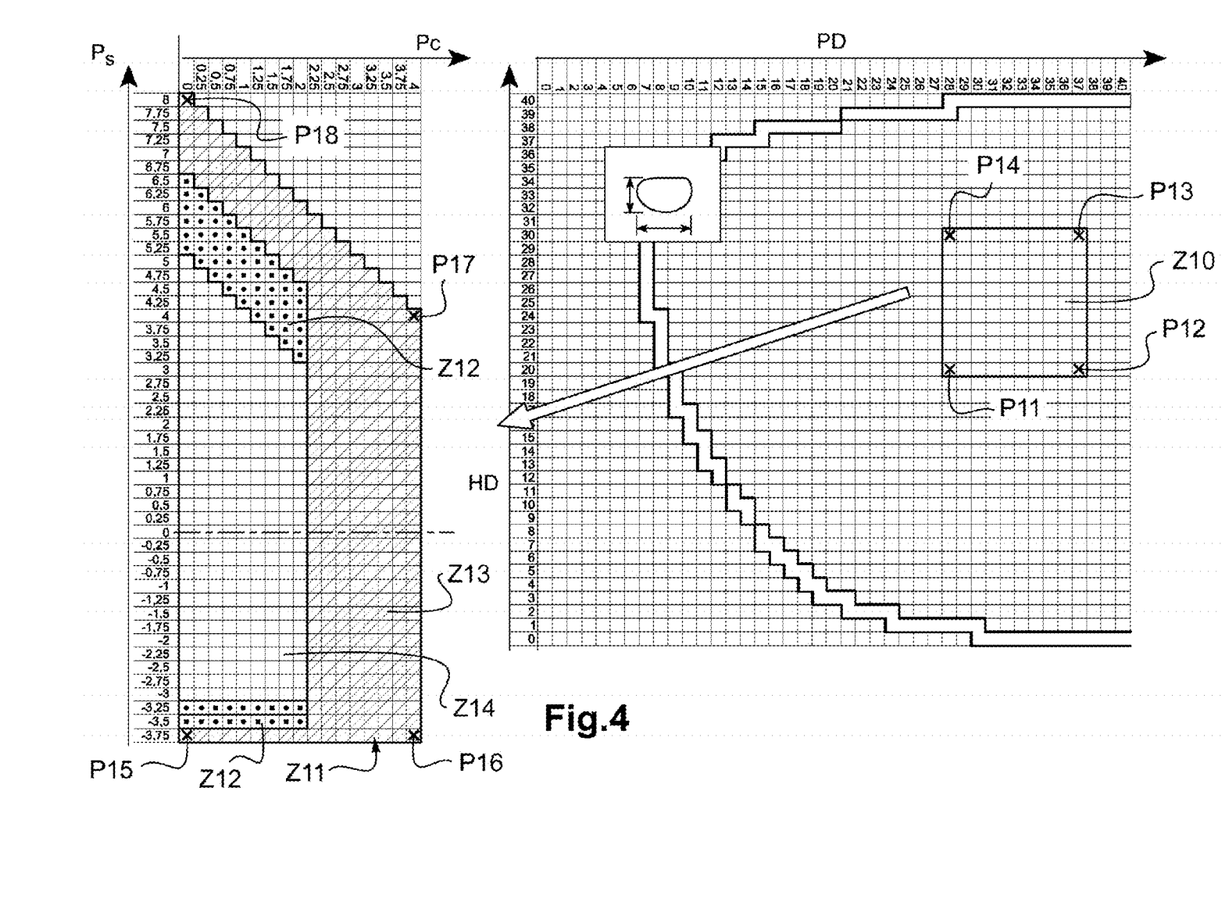
FIG. 4 represents two graphs illustrating the ranges of the first and second parameters used in the context of the testing process from FIG. 3.

This first range Z10, clearly illustrated on the right-hand part of FIG. 4, corresponds to a range of doublets of values within which it is desired for the pair of spectacles to be feasible.

Here, the first parameters are the pupillary height HD and the half-pupillary distance PD. Each doublet then comprises, on the x-axis, a half-pupillary distance PD value and, on the y-axis, a pupillary height HD value.

In this second embodiment of the testing process, it is desired for the pupillary height HD and half-pupillary distance PD values to not be discriminating when the spectacle frame 10 is chosen by a customer (as long as these values remain included in the first range Z10).

In FIG. 2, it is observed that the first range Z10 is between four end points P11, P12, P13, P14.

Here, by way of illustration, these four end points P11, P12, P13, P14 are defined in the following manner:
at point P11, HD=20 mm and PD=28 mm,
at point P12, HD=20 mm and PD=37 mm,
at point P13, HD=30 mm and PD=37 mm,
at point P14, HD=30 mm and PD=28 mm.

This first range Z10 then comprises all the doublets (HD, PD) located in the square, the corners of which correspond to the four end points P11, P12, P13, P14.

Here, the first range Z10 is here discretized by intervals of 1 mm.

During step b) (denoted Sb in FIG. 3), the calculator acquires the second range Z11.

This second range Z11, clearly illustrated on the left-hand part of FIG. 4, corresponds to a range of doublets of values within which it is desired to verify whether or not the pair of spectacles is feasible.

Here, the second parameters are the cylindrical refractive power Pc and the spherical refractive power Ps. Each doublet then comprises, on the x-axis, a cylindrical power Pc value and, on the y-axis, a spherical refractive power Ps value.

In this second embodiment of the testing process, it is desired specifically to be able to determine, in this second range Z11, which are the doublets of values (Ps, Pc) for which it will be possible to fit an ophthalmic lens in the spectacle frame 10, irrespective of the values of the doublets (HD, PD) included in the first range Z10.

In FIG. 4, it is observed that the second range Z11 is between four end points P15, P16, P17, P18.

Here, by way of illustration, these four end points P15, P16, P17, P18 are defined in the following manner:
at point P15, Pc=0 $\delta$ and Ps=−3.75 $\delta$,
at point P16, Pc=4 $\delta$ and Ps=−3.75 $\delta$,
at point P17, Pc=4 $\delta$ and Ps=4 $\delta$,
at point P18, Pc=0 $\delta$ and Ps=8 $\delta$.

This second range Z11 then comprises all the doublets (Ps, Pc) located in the quadrilateral, the corners of which correspond to the four end points P15, P16, P17, P18.

The second range Z11 is here discretized by intervals of 0.25 $\delta$.

As for step c), it is performed in several successive and iterative operations.

This step consists in evaluating, for each discretized point of the second range Z11, a degree of feasibility Nf of the pair of spectacles.

This degree of feasibility will here too take three different values, depending on whether the pair of spectacles is feasible, is not feasible, or is feasible on condition that fitting imperfections are accepted.

During this step c), the calculator will scan all the discretized points of the second range Z11, each time calculating the value of this degree of feasibility Nf.

For this, unlike the process carried out in the first embodiment, here this step c) is carried out in two substeps, depending on whether the spherical power Ps value of the points $P_i$ to be examined is positive or negative.

It will be possible here to consider only the case of the points $P_i$ to be examined for which the spherical power Ps is positive (boxed portion of the flow chart from FIG. 3). The implementation of the process for the other points to be examined will indeed be carried out in a homologous manner.

The first operation Sc1 of step c) consists in determining the point $P_i$ to be examined, among the discretized points of the second range Z11. This point $P_i$ comprises coordinates denoted ($Pc_i$, $Ps_i$).

Initially (for i=0), the coordinates ($Pc_0$, $Ps_0$) of the point $P_0$ are coincident with those of the end point P18.

The second operation Sc2 consists in determining whether, for this point $P_i$ to be examined, the fitting of an ophthalmic lens in the spectacle frame 10 is possible irrespective of the pupillary height HD and half-pupillary distance PD included in the first range Z10.

In practice, this second operation Sc2 is carried out by calculating whether this fitting is possible when the pupillary height HD and half-pupillary distance PD are equal to the coordinates of the end point P11, then to those of the end point P12, then to those of the end point P13, and finally to those of the end point P14.

Each of these four calculations is carried out by means of a mathematical function f, which depends on:
the shape of the eye wire 11 of the spectacle frame,
the spherical refractive power Ps and cylindrical refractive power Pc values at the point $P_i$ to be examined,
the pupillary height HD and half-pupillary distance PD values at the end point in question, and
on the type of material used for the manufacture of the lenses.

The result of this function f makes it possible to obtain the degree of feasibility Nf of the pair of spectacles at the point $P_i$ to be examined.

This degree of feasibility Nf may be equal to zero, which then means that it is not a priori possible to assemble to the spectacle frame 10 an ophthalmic lens having a spherical refractive power Ps and a cylindrical refractive power Pc having values that correspond to the coordinates of the point $P_i$ to be examined, irrespective of the pupillary height HD and half-pupillary distance PD values included in the first range Z10.

The degree of feasibility Nf may be equal to one, which then means that it is a priori possible to assemble such a pair of spectacles, on condition that the user is willing to accept an assembly that is imperfect (in esthetic terms or in terms of solidity of assembly).

Finally, the degree of feasibility may be equal to two, which then means that it is a priori possible to assemble such a pair of spectacles, while ensuring a perfect assembly.

The third operation Sc3 consists in testing if the coordinates of the point $P_i$ to be examined are equal to (4 δ, 0 δ).

If this is not the case, the calculator performs an operation Sc4 that consists in incrementing the subscript i. The step Sc1 and the following steps may then be repeated, by considering at step Sc1 a new point $P_{i+1}$ to be examined.

The defining of this new point $P_{i+1}$ consists in:
incrementing by 0.25 δ the cylindrical power Pc as long as the side of the quadrilateral has not been reached, or in
decrementing by 0.25 δ the spherical power Ps and bringing the cylindrical power Pc to 0 δ if the side of the quadrilateral has been reached.

At the end of the operation Sc3, if the coordinates of the point $P_i$ to be examined are equal to (4 δ, 0 δ), the calculator performs an operation Sc5 of waiting for all the points Pi to have been examined and it triggers a timeout.

The examination of the points for which the spherical power Ps is negative is indeed performed at the same time as the examination of the points for which the spherical power Ps is positive; it is then necessary to wait for all the calculations to end.

If all the calculations are carried out before the end of the timeout, the calculator stores all the results in its random-access memory (Sc6 operations).

If all the calculations are not carried out before the end of the timeout (which indicates that there is a problem), the calculator interrupts the process (Sc7 operations).

It will be noted here that in order to reduce the number of calculations to be carried out, the calculator could, when a point Pi to be examined has a degree of feasibility Nf equal to zero, allocate the value 0 to the degree of feasibility Nf of each of the points of the second range Z11 of which:
the Ps y-coordinate is equal to the $Ps_i$ y-coordinate of the point $P_i$ to be examined, and of which
the Pc x-coordinate is greater than the Pc x-coordinate of the point $P_i$ to be examined.

For the same purpose, the calculator could also, when a point $P_i$ to be examined has a degree of feasibility Nf equal to zero, allocate the value 0 to the degree of feasibility Nf of each of the points $P_k$ of the second range Z11 of which:
the $Pc_k$ x-coordinate is equal to the sum of a multiple of the increment (0.25 δ) and of the Pc x-coordinate of the point $P_i$ to be examined, and of which
the $Ps_k$ y-coordinate is equal to the $Ps_i$ y-coordinate of the point $P_i$ to be examined, minus the same multiple of the increment (0.25 δ), which may be written:
Nf $(P_k)$=0 if $Ps_k$=$Ps_i$−k·0.25 and if $Pc_k$=$Pc_i$+k·0.25

Finally, it could be noted that the values of the end points P11, P12, P13, P14 delimiting the first range Z10 could be determined either randomly, according to the wishes of the user, or automatically, on the basis of geomorphological data relating to a given region of the globe.

Indeed, it is observed that the average half-pupillary distances and pupillary heights vary from one region of the globe to another.

In that case, during a step prior to step a), the calculator could perform a step of acquiring average values of the half-pupillary distances and of the pupillary heights in the region where the sale of the spectacle frame will take place, then, in step a), it could determine the values of the coordinates of the end points P11, P12, P13, P14 as a function of these average values.

Figure 5:
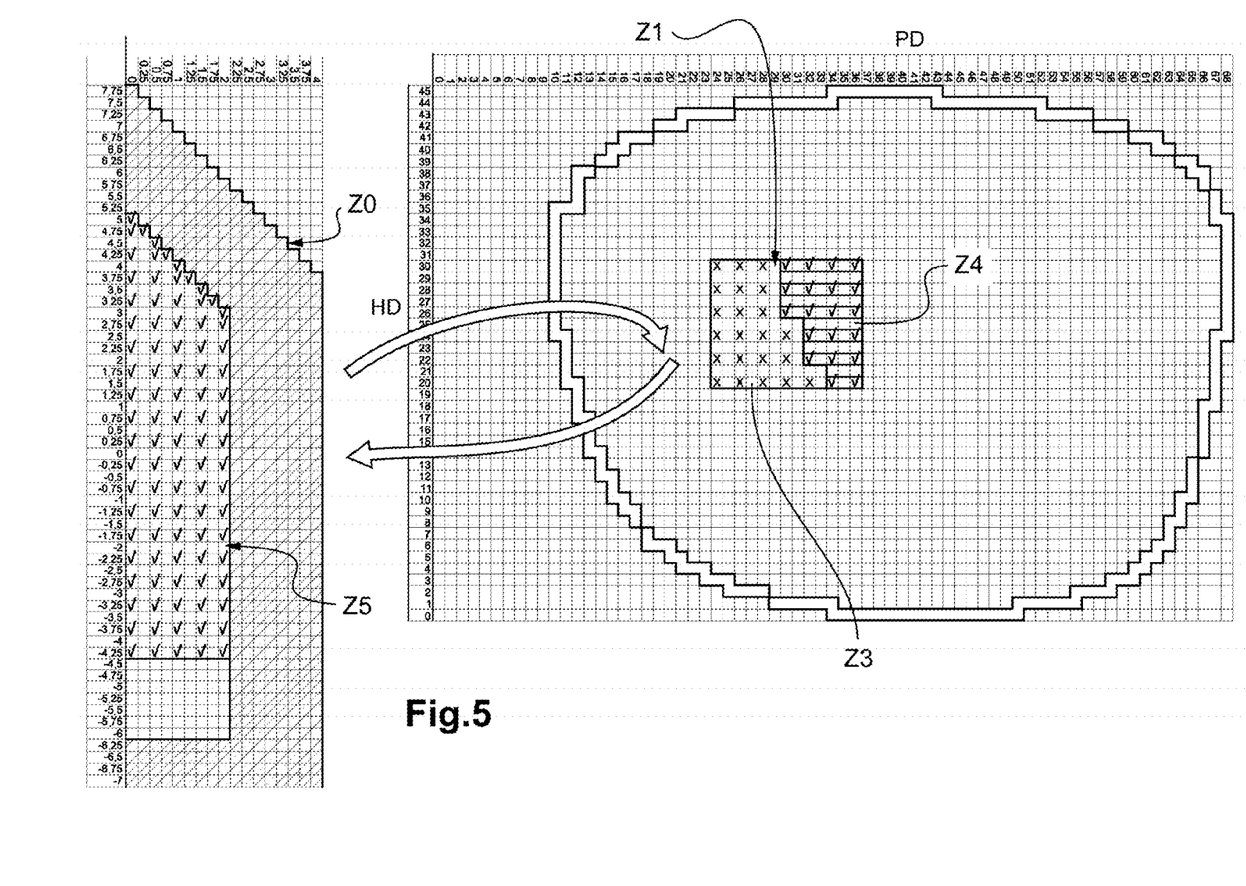
FIG. 5 represents two graphs illustrating the ranges of the first and second parameters used in the context of a third embodiment of a testing process in accordance with the invention.

A third embodiment of the testing process in accordance with the invention may also be described, with reference to FIG. 5.

In this third embodiment, the objective will consist, when the degree of feasibility Nf of the pair of spectacles is equal to zero at a point $P_i$ to be examined, in verifying if it could not be equal to 2 if the first range were reduced. A subrange of the first range will therefore be sought for which all the degrees of feasibility Nf of the points of the second range will be equal to 2.

The implementation of this third embodiment of the testing process will be carried out in the following manner.

The first operation carried out by the calculator consists in implementing the first embodiment of the process described above, by considering however that the degree of feasibility Nf of the pair of spectacles is either equal to zero (if the pair of spectacles is not feasible), or equal to two (if the pair of spectacles is feasible).

As shown in FIG. 5, the second range Z1 then comprises a zone Z4 in which the pair of spectacles is feasible, and a second zone Z3 in which the pair of spectacles is not feasible.

For the points of this second zone Z3, it will then be sought to determine among the discretized points of the first range Z0 those for which the assembly of the pair of spectacles would be feasible.

Specifically, at the end of the first embodiment of the testing process, it is known that if the pupillary height HD and half-pupillary distance PD of the wearer are included in the zone Z4 of the second range Z1 and if the spherical refractive power Ps and cylindrical refractive power Pc are included in the first range Z0, it will be possible to assemble the pair of spectacles without a defect.

This time, the process will be supplemented by a fourth step d) that makes it possible to determine, in the first range Z0, the points for which the pair of spectacles will be feasible when the pupillary height HD and half-pupillary distance PD of the wearer are included in the zone Z3 of the second range Z1.

In practice, this step d) will consist, for the calculator, in implementing the second embodiment of the testing process illustrated in FIGS. 3 and 4.

It will thus be possible to determine, in the first range Z0, a zone Z5 (or "subrange") throughout which the pair of spectacles will be feasible, irrespective of the pupillary height HD and half-pupillary distance PD values included in the second range Z1.

As a variant, it would have been possible to reverse the steps, by firstly implementing the second embodiment of the testing process illustrated in FIGS. 3 and 4, then by implementing, during a step d), the first embodiment of the testing process illustrated in FIGS. 1 and 2.

A fourth embodiment of the testing process in accordance with the invention may finally be described, which is not illustrated in the figures.

In this fourth embodiment, the objective will consist, when the degree of feasibility Nf of the pair of spectacles is equal to 2 at a point $P_i$ to be examined, in verifying if it could not also be equal to 2 if the first range were enlarged. An "overrange" that encompasses the first range will therefore be sought in which all the points that had a degree of feasibility Nf equal to 2 will retain this degree of feasibility Nf.

The implementation of this fourth embodiment of the testing process will be carried out in the following manner.

The first operation carried out by the calculator consists here too in implementing the first embodiment of the process described above, by considering however that the degree of feasibility Nf of the pair of spectacles is either equal to zero (if the pair of spectacles is not feasible), or equal to two (if the pair of spectacles is feasible).

The second range Z1 then comprises a zone Z4 in which the pair of spectacles is feasible, and a second zone Z3 in which the pair of spectacles is not feasible.

This time, the process will be supplemented by a fourth step d) that makes it possible to determine, in an overrange encompassing the first range Z0, the points in which the pair of spectacles would be feasible when the pupillary height HD and half-pupillary distance PD of the wearer are included in the zone Z4 of the second range Z1.

In practice, this step d) will consist, for the calculator, in implementing the second embodiment of the testing process illustrated in FIGS. 3 and 4.

It will thus be possible to determine, in the overrange encompassing the first range Z0, a zone throughout which the pair of spectacles will be feasible, irrespective of the pupillary height HD and half-pupillary distance PD values included in the zone Z2 of the second range Z1.

Whatever embodiment is used, the testing process makes it possible to determine a zone of the first range Z0 and a zone of the second range Z1 in which the assembly of the pair of spectacles will be possible.

This testing method will then be able to be repeated with other spectacle frames 10, so as to obtain a catalogue of spectacle frames in which it will be easy to determine the spectacle frames that will be able to be offered to a wearer, considering his/her prescriptions.

It is for this purpose that the database register stored in the read-only memory of the calculator could be used, remembering that this database register comprises several entries each associating, with a spectacle frame 10 reference, first and second ranges.

More specifically, after having implemented the testing process on a spectacle frame 10 of a new reference, the calculator will be able to record (in a new entry of the database associated with said new reference) data relating to the validated zones of the first and second ranges Z0, Z1 (those in which the assembly of the pair of spectacles is possible).

The case of an optician making several spectacle frames, each referenced in the database register, available to his/her customers may now be considered.

In that case, when a new wearer appears with his/her prescriptions (spherical and cylindrical refractive power, pupillary height and half-pupillary distance), the optician will be able to enter these prescriptions on the acquisition means of the calculator, so that the calculator can carry out an operation of selecting database entries for which the prescriptions are included in the validated zones of the first and second ranges Z0, Z1.

In this way, the optician will be able to communicate to the wearer which spectacle frames he/she will be able to choose while being certain of obtaining a good assembly quality, which spectacle frames he/she will be able to choose if he/she is willing to accept an average assembly quality, and which spectacle frames he/she will not be able to choose.

In order to easily indicate which spectacle frames the wearer will be able to choose, provision could be made for the optician to provide the wearer with either an electronic catalogue of spectacle frames, or for the optician to convey an indicator of feasibility to the wearer.

Consider firstly the case of the electronic catalogue.

In practice, the optician will make a computer available to the wearer which has access to the entries of the database register for which the prescriptions are included in the validated zones of the first and second ranges Z0, Z1.

To make this catalogue pleasant to consult, provision could be made for each entry to store an identifier of the spectacle frame (for example the name of the model of the frame) and at least one photo of the spectacle frame associated with this entry.

Consider now the case of the indicator of feasibility.

Provision could be made for the optician, each time that he/she puts a new spectacle frame on display, to affix thereto an indicator of feasibility (for example in the form of a grade between 1/10 and 10/10, or a colored sticker). This indicator of feasibility will be previously determined as a function of the validated zones of the first and second ranges Z0, Z1 (for example as a function of their amplitudes or as a function of their values).

Thus, after the optician has entered the prescriptions of the wearer into the calculator, the latter will be able to calculate what indicators of feasibility the wearer will have access to.

By way of example, a wearer needing a low spherical power and a zero cylindrical power might have access to all the frames having a grade between 1/10 and 10/10, whereas a wearer needing a high spherical power and a high cylindrical power might only have access to the frames having a grade between 9/10 and 10/10.

The invention claimed is:

1. A process for testing the feasibility of a pair of spectacles including an identified spectacle frame, the process comprising:

acquiring, at a processor, a first range of values of at least two first parameters relating to a spectacle wearer by at least one input device, the at least two first parameters including at least one refractive power of an ophthalmic lens for the pair of spectacles, the first range of values including a plurality of points corresponding to doublets of values of the at least two first parameters, the first range of values including a first zone within which the pair of spectacles is feasible, the first zone encompassing first corner points of the first plurality of points and other first points within a first area between the first corner points;

acquiring, at the processor, a second range of values of at least two second parameters relating to a spectacle wearer by the at least one input device, the at least two second parameters being different from each of the at least two first parameters, the at least two second parameters being at least one of a pupillary height and a half-pupillary distance related to the spectacle wearer, the second range of values including a second zone within which the pair of spectacles is feasible, the second zone encompassing second corner points of the second plurality of points and other second points within a second area between the second corner points; and verifying, for a characteristic number of values of each of the second parameters, that the pair of spectacles is feasible irrespective of the value of each of the first parameters included in the second range in order to verify a priori a possibility of assembling the pair of spectacles, when the wearer is not yet identified; and outputting a verification result of the verifying that the pair of spectacles is feasible to manufacture the pair of spectacles.

2. The testing process as claimed in claim 1, wherein said first and second parameters are ophthalmic, morphological or geometric-morphological parameters characterizing spectacle wearers.

3. The testing process as claimed in claim 2, wherein said at least two first and at least two second parameters are chosen from:
a spherical refractive power,
a cylindrical refractive power,
a pupillary height, and
a pupillary distance or half-pupillary distance.

4. The testing process as claimed in claim 3, wherein:
in the acquiring the first range of values, a range of values of the at least two first parameters is acquired, and
in the verifying, it is verified, for a characteristic number of values of each of the at least two second parameters, that the pair of spectacles is feasible irrespective of the values of the at least two first parameters included in the two first parameters range.

5. The testing process as claimed in claim 3, wherein:
in the acquiring the first range of values, a range of values of the at least two second parameters is acquired, and
in the verifying, it is verified, for a characteristic number of pairs of values of the at least two second parameters, that the pair of spectacles is feasible irrespective of the values of the at least two first parameters included in the first range.

6. The testing process as claimed in claim 3, wherein, in the verifying, a degree of feasibility of the pair of spectacles is evaluated, said degree of feasibility taking at least three different values.

7. The testing process as claimed in claim 2, wherein:
in the acquiring the first range of values, a range of values of the at least two first parameters is acquired, and
in the verifying, it is verified, for a characteristic number of values of each of the at least two second parameters, that the pair of spectacles is feasible irrespective of the values of the at least two first parameters included in the two first parameters range.

8. The testing process as claimed in claim 2, wherein:
in the acquiring the first range of values, a range of values of the at least two second parameters is acquired, and
in the verifying, it is verified, for a characteristic number of pairs of values of the at least two second parameters, that the pair of spectacles is feasible irrespective of the values of the at least two first parameters included in the first range.

9. The testing process as claimed in claim 2, wherein, in the verifying, a degree of feasibility of the pair of spectacles is evaluated, said degree of feasibility taking at least three different values.

10. The testing process as claimed in claim 1, wherein:
in the acquiring the first range of values, a range of values of the at least two first parameters is acquired, and
in the verifying, it is verified, for a characteristic number of values of each of the at least two second parameters, that the pair of spectacles is feasible irrespective of the values of the at least two first parameters included in the two first parameters range.

11. The testing process as claimed in claim 10, wherein:
in the acquiring the first range of values, a range of values of the at least two second parameters is acquired, and
in the verifying, it is verified, for a characteristic number of pairs of values of the at least two second parameters, that the pair of spectacles is feasible irrespective of the values of the at least two first parameters included in the first range.

12. The testing process as claimed in claim 1, wherein:
in the acquiring the first range of values, a range of values of the at least two second parameters is acquired, and
in the verifying, it is verified, for a characteristic number of pairs of values of the at least two second parameters, that the pair of spectacles is feasible irrespective of the values of the at least two first parameters included in the first range.

13. The testing process as claimed in claim 1, wherein, in the verifying, a degree of feasibility of the pair of spectacles is evaluated, said degree of feasibility taking at least three different values.

14. The testing process as claimed in claim 1, wherein, prior to the acquiring the first range of values, acquiring curvature data of the spectacle frame, the at least two first parameters being a spherical refractive power or cylindrical refractive power, the first range of values of the at least two first parameters being chosen as a function of said curvature data of the spectacle frame.

15. The testing process as claimed in claim 1, wherein, considering a subrange of the range of values of each of the at least two second parameters in which the pair of spectacles is not feasible, further comprising:
verifying, for a characteristic number of values of each of the at least two first parameters, that the pair of spectacles is feasible irrespective of the value of each of the at least two second parameters included in said subrange.

16. The testing process as claimed in claim 1, wherein, considering a subrange of the range of values of each of the at least two second parameters in which the pair of spectacles is feasible and a subrange encompassing the range of values of the at least two first parameters, further comprising:
verifying, for a characteristic number of values of the at least two first parameters included in said subrange, that the pair of spectacles is feasible irrespective of the value of each of the at least two second parameters included in said subrange.

17. A method for classifying spectacle frames, by a database including entries each associated with a spectacle frame, the method comprising:
a computing operation during which the testing process as claimed in claim 1 is carried out by a calculator comprising a processor and a memory for an identified spectacle frame; and
a storage operation during which the first range of values of each of the at least two first parameters and a range of values of each of the at least two second parameters in the whole of which the pair of spectacles is feasible is recorded in a new entry of the database associated with said identified spectacle frame.

18. The classifying method as claimed in claim 17, further comprising:
acquiring a first particular value of the at least two first parameters and a second particular value of the at least two second parameters, the first and second values corresponding to a specific spectacle wearer; and
selecting entries of said database in which the stored ranges comprise said first and second particular values.

19. A catalogue of spectacle frames available for manufacturing pairs of spectacles, the catalogue comprising:

for each spectacle frame:
an identifier of the spectacle frame,
a first range of values of at least two first parameters relating to a spectacle wearer acquired by at least one input device, the at least two first parameters including at least one refractive power of an ophthalmic lens for the pair of spectacles, the first range of values including a plurality of points corresponding to doublets of values of the at least two first parameters, the first range of values including a first zone within which the pair of spectacles is feasible, the second zone encompassing first corner points of the first plurality of points and other first points within a first area between the first corner points, and
a second range of values of at least two second parameters relating to a spectacle wearer acquired by the at least one input device, the at least two second parameters being different from each of the at least two first parameters, the at least two second parameters being at least one of a pupillary height and a half-pupillary distance related to the spectacle wearer, the second range of values including a second zone within which the pair of spectacles is feasible, the second zone encompassing second corner points of the second plurality of points and other second points within a second area between the second corner points,
said first and second ranges of values being defined such that it is verified that it is possible to manufacture a pair of spectacles with said spectacle frame irrespective of the values of the first and second parameters included in the first and second ranges.

20. An indicator of feasibility of a pair of spectacles by an identified spectacle frame, the indicator comprising:
a physical indication configured to be affixed to the pair of spectacles and being one of a grade indicator and a sticker, the physical indication being determined by acquiring a first range of values of at least two first parameters relating to a spectacle wearer by at least one input device, the at least two first parameters including at least one refractive power of an ophthalmic lens for the pair of spectacles, the first range of values including a plurality of points corresponding to doublets of values of the at least two first parameters, the first range of values including a first zone within which the pair of spectacles is feasible, the second zone encompassing first corner points of the first plurality of points and other first points within a first area between the first corner points, and
acquiring a second range of values of at least two second parameters relating to a spectacle wearer by the at least one input device, the at least two second parameters being different from each of the at least two first parameters, the at least two second parameters being at least one of a pupillary height and a half-pupillary distance related to the spectacle wearer, the second range of values including a second zone within which the pair of spectacles is feasible, the second zone encompassing second corner points of the second plurality of points and other second points within a second area between the second corner points,
said first and second ranges of values being defined such that it is verified that it is possible to manufacture a pair of spectacles with said spectacle frame irrespective of the values of the first and second parameters included in the first and second ranges,
wherein the physical indication is determined as a function of the first and second zones of the first and second ranges that are verified as being feasible.

* * * * *